(12) United States Patent
Sato (10) Patent No.: US 10,107,885 B2
(45) Date of Patent: Oct. 23, 2018

(54) PULSE DETECTION APPARATUS AND PULSE DETECTION METHOD

(71) Applicant: KYUSHU INSTITUTE OF TECHNOLOGY, Kitakyushu-shi (JP)

(72) Inventor: Yasushi Sato, Kitakyushu (JP)

(73) Assignee: KYUSHU INSTITUTE OF TECHNOLOGY, Kitakyushi-shi (JP)

( * ) Notice: Subject to any disclaimer, the term of this patent is extended or adjusted under 35 U.S.C. 154(b) by 703 days.

(21) Appl. No.: 14/439,474

(22) PCT Filed: Nov. 19, 2013

(86) PCT No.: PCT/JP2013/081163
§ 371 (c)(1),
(2) Date: Apr. 29, 2015

(87) PCT Pub. No.: WO2014/080905
PCT Pub. Date: May 30, 2014

(65) Prior Publication Data
US 2015/0346306 A1    Dec. 3, 2015

(30) Foreign Application Priority Data
Nov. 20, 2012   (JP) .................................. 2012-253838

(51) Int. Cl.
*G01R 33/563* (2006.01)
*G01R 33/60* (2006.01)
(Continued)

(52) U.S. Cl.
CPC .......... *G01R 33/5635* (2013.01); *A61B 5/024* (2013.01); *A61B 5/055* (2013.01);
(Continued)

(58) Field of Classification Search
None
See application file for complete search history.

(56) References Cited

U.S. PATENT DOCUMENTS

| 5,323,776 A * | 6/1994 | Blakeley | A61B 5/02416 |
| | | | 128/901 |
| 6,407,548 B1 * | 6/2002 | Dietz | G01R 33/3854 |
| | | | 324/309 |

(Continued)

FOREIGN PATENT DOCUMENTS

| JP | 11-47131 A | 2/1999 |
| JP | 2002-65677 A | 3/2002 |

(Continued)

OTHER PUBLICATIONS

International Search Report dated Dec. 17, 2013 in PCT/JP13/081163 Filed Nov. 19, 2013.

*Primary Examiner* — Melissa Koval
*Assistant Examiner* — Nasima Monsur
(74) *Attorney, Agent, or Firm* — Oblon, McClelland, Maier & Neustadt, L.L.P.

(57) ABSTRACT

Provided is a pulse detection apparatus and a pulse detection method less susceptible to movement of a subject and less susceptible to noise. An oscillation frequency controller is configured to cause a frequency variable oscillator to oscillate at a predetermined oscillation frequency, which is a frequency within a range assumed as a resonance frequency of a molecule of a predetermined constituent constituting the blood flowing through a human body. The oscillation frequency controller also controls an oscillation frequency based on a phase difference signal and an amplitude signal, wherein the phase difference signal indicates the phase difference between a transmission signal transmitted from an antenna to the human body and a reception signal received by the antenna, and the amplitude signal indicates the magnitude of the amplitude of the received signal. A pulse detector detects the change of the amplitude signal in an amplitude direction as a pulse signal.

7 Claims, 8 Drawing Sheets

(51) Int. Cl.
  *G01R 33/34* (2006.01)
  *A61B 5/024* (2006.01)
  *A61B 5/055* (2006.01)
  *G01R 33/36* (2006.01)
  *A61B 5/00* (2006.01)
  *A61B 5/18* (2006.01)
  *G01R 33/341* (2006.01)

(52) U.S. Cl.
  CPC ... G01R 33/34092 (2013.01); G01R 33/3607 (2013.01); G01R 33/60 (2013.01); *A61B 5/18* (2013.01); *A61B 5/6891* (2013.01); *A61B 5/6893* (2013.01); *G01R 33/341* (2013.01)

(56) References Cited

U.S. PATENT DOCUMENTS

| | | | |
|---|---|---|---|
| 6,552,634 B1* | 4/2003 | Raab | H03F 1/0205 330/124 R |
| 2007/0265522 A1* | 11/2007 | Kassai | A61B 5/055 600/411 |
| 2009/0203988 A1 | 8/2009 | Phua et al. | |
| 2009/0322330 A1* | 12/2009 | Adachi | G01R 33/5659 324/309 |
| 2010/0145420 A1* | 6/2010 | Zhu | A61B 5/055 607/103 |
| 2010/0321232 A1* | 12/2010 | Lewis | G01S 13/50 342/160 |
| 2011/0227574 A1* | 9/2011 | Akita | G01R 33/3692 324/322 |
| 2012/0223709 A1* | 9/2012 | Schillak | G01R 33/3607 324/309 |
| 2013/0043886 A1 | 2/2013 | Mase et al. | |

FOREIGN PATENT DOCUMENTS

| | | |
|---|---|---|
| JP | 2009-528081 A | 8/2009 |
| WO | 2011/099600 A1 | 8/2011 |

* cited by examiner

PULSE DETECTION APPARATUS AND PULSE DETECTION METHOD

TECHNICAL FIELD

The present invention relates to a pulse detection apparatus and a pulse detection method preferably applicable to, for example, a medical device, an in-vehicle biosensor and the like.

BACKGROUND ART

Conventionally, a method for detecting a change in volume of a blood vessel resulting from fluctuations and a method for detecting a change in pressure in the blood vessel are known as methods for measuring a pulse. The change in the volume of the blood vessel resulting from fluctuations is typically detected by using an optical method, while the change in the pressure in the blood vessel is typically detected by using a piezoelectric method. In the optical method, a living body is irradiated with a light in a wavelength range of the hemoglobin contained in the blood, and the strength of the transmitted light or reflected light is converted into an electrical signal to thereby detect the pulse. In the piezoelectric method, a piezoelectric sensor is pressed against an artery, and a voltage obtained by the piezoelectric sensor is detected as the pulse.

However, in both the optical method and the piezoelectric method, since it is required to mount the sensor to the body of a subject, the movement of the body of subject will be limited to some extent. Particularly, in the piezoelectric method, in order to perform precise measurement, it is required to employ a pressing means to correctly press the piezoelectric sensor on directly above the artery, and therefore not only the movement of the body of the subject, but also the environment for performing measurement will be considerably limited.

To solve such a problem, a method has been proposed in which the pulse can be detected in a non-contact manner without directly contacting the body of the human body with the sensor. The non-contact detection is often performed by using a Doppler method. In the Doppler method, the living body is irradiated with a microwave, and the reflected wave from the living body is received; the difference between the oscillation frequency and the reception frequency is converted into an acoustic signal to thereby detect the blood flow. For example, Patent Document 1 describes an ultrasonic diagnostic image processing device using the Doppler method.

CITATION LIST

Patent Literature

Patent Document 1: Japanese Unexamined Patent Application Publication No. H11-47131

SUMMARY OF INVENTION

Technical Problem

In the Doppler method, a frequency deviation caused by relative movement between the heart (which is the object-to-be-observed) and the sensor (which senses the heart) is detected. Therefore, the frequency deviation between the oscillation frequency and the reception frequency occurs not only when the heart moves, but also when the sensor itself (which detects the movement of the heart) moves, for example. In other words, there is a possibility that, if other movement than the movement of the heart, which is originally required, occurs, the other movement will be erroneously detected as a pulse signal.

Solution to Problem

The present invention is made to solve the aforesaid problems, and an object of the present invention is to provide a pulse detection apparatus and a pulse detection method less susceptible to movement of a subject and less susceptible to noise caused by the movement of the body of the subject.

To solve the problems, the pulse detection apparatus of the present invention includes a magnetic-field application unit, an antenna, a signal separator, a phase comparator, an amplitude detector, an oscillation frequency controller, and a pulse detector. Each component has the following configuration and function. The magnetic-field application unit is to be arranged near a human body to apply a predetermined magnetic field to the human body. The frequency variable oscillator is configured to oscillate at a predetermined oscillation frequency. The predetermined oscillation frequency is a frequency within a range assumed as a resonance frequency of a molecule of a predetermined constituent constituting the blood flowing through the human body. The antenna is to be arranged near the human body. The antenna is configured to transmit a signal oscillated by the frequency variable oscillator, as a radio wave, and receive a radio wave reflected by the human body and then returned to the antenna. The signal separator is configured to separate a transmission signal from a reception signal, wherein the transmission signal is transmitted from the antenna, and the reception signal is received by the antenna. The phase comparator is configured to compare the phase of the transmission signal with the phase of the reception signal and output a phase difference signal. The amplitude detector is configured to detect the amplitude of the reception signal and output an amplitude signal. The oscillation frequency controller is configured to control the oscillation frequency based on the phase difference signal and the amplitude signal. The pulse detector is configured to detect the change of the amplitude signal in an amplitude direction as a pulse signal.

In the pulse detection method of the present invention first a predetermined magnetic field is applied to the human body. Thereafter, a frequency variable oscillator is caused to oscillate at a predetermined frequency. The predetermined oscillation frequency is a frequency within a range assumed as a resonance frequency of a molecule of a predetermined constituent constituting a blood flowing through the human body. Thereafter, a signal oscillated by the frequency variable oscillator is transmitted as a radio wave from an antenna arranged near the human body, and a radio wave reflected by the human body and then returned to the antenna is received. Thereafter, a transmission signal is separated from a reception signal, wherein the transmission signal is transmitted from the antenna, and the reception signal is received by the antenna. Thereafter, the phase of the transmission signal is compared with the phase of the reception signal, and a phase difference signal is outputted. Thereafter, the amplitude of the reception signal is detected, and an amplitude signal is outputted. Thereafter, the oscillation frequency is controlled based on the phase difference signal and the amplitude signal. Thereafter, the change of the amplitude signal in an amplitude direction is detected as a pulse signal.

By configuring the pulse detection apparatus and performing the pulse detection process in the aforesaid manner, the resonance frequency of the molecules of the predetermined constituent constituting the blood flowing through the human body can be detected, and the change of the detected resonance frequency in the amplitude direction is detected as the pulse signal.

Advantageous Effects of Invention

The present invention provides a pulse detection apparatus and a pulse detection method less susceptible to movement of the subject and less susceptible to noise caused by the movement of the body of the subject.

DESCRIPTION OF EMBODIMENTS

An example of a pulse detection apparatus according to an embodiment of the present invention will be described in the order below while referring to the drawings. However, the present invention is not limited to this example.
1. Configuration Example of Pulse Detection Apparatus
2. Various Modifications
[1. Configuration Example of Pulse Detection Apparatus]

Figure 1:
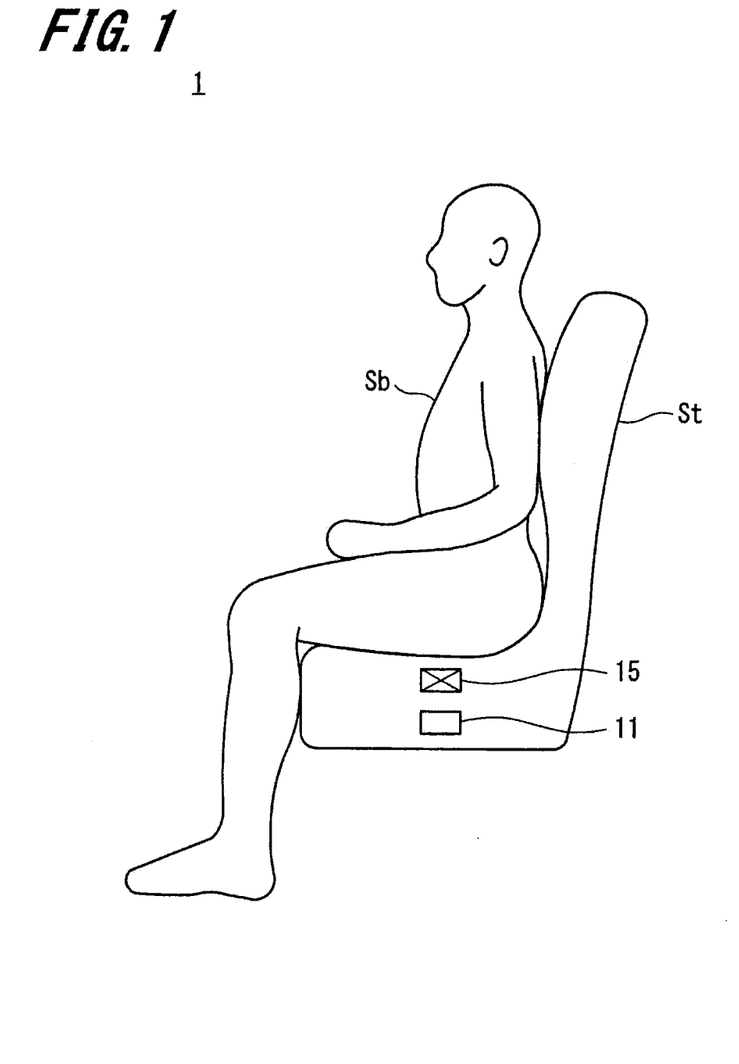
FIG. 1 is a view showing an exemplary use of a pulse detection apparatus according to an embodiment of the present invention.

FIG. 1 is a view showing an exemplary use of a pulse detection apparatus 1 according to an embodiment of the present invention. FIG. 1 exemplifies an arrangement around a seat when the pulse detection apparatus of the present invention is applied to an in-vehicle device adapted to sense doze and degree of fatigue of the driver. As shown in FIG. 1, the pulse detection apparatus 1 includes a loop antenna 15 and a magnet 11 that serves as a magnetic-field application unit, wherein the loop antenna 15 is arranged below a seat St in the vehicle, and the magnet 11 is arranged below the loop antenna 15. The loop antenna 15 irradiates the body of a subject Sb seated on the seat St with a radio wave, and receives the radio wave reflected by the subject Sb and then returned to the loop antenna 15. The magnet 11 applies a predetermined magnetic field to the body of the subject Sb seated on the seat St. Incidentally, other components configuring the pulse detection apparatus 1, such as a VCO (Voltage Controlled Oscillator), which generates a signal of an oscillation frequency supplied to the loop antenna 15, are not shown in FIG. 1. Details of these components will be described later with reference to FIG. 2.

The pulse detection apparatus 1 according to the embodiment of the present invention uses a technique of ESP (Electron Spin Resonance) to detect the change of a vibration (a pulse wave) generated on the vessel wall of an artery and to output a pulse signal, which indicates the change of the pulse wave. The ESR is adapted to observe a resonance phenomenon generated in association with the transition of electron spins of an unpaired electrons in a substance.

When an unpaired electron in the substance is placed in a magnetic field, the direction of the electron spin will align parallel to or anti-parallel to the direction of the magnetic field, according to the value of spin amount (magnetic moment) of the unpaired electron. At this time, the energy level of the electron spin is split into two by the spin amount (the Zeeman splitting). When energy equivalent to the difference between the two energy levels is added from the outside, the electron spin with low energy will absorb the added energy to thereby transition to a spin with high energy. By sensing the amount of the energy absorbed by the electron spin at this time, it is possible to obtain an ESR spectrum; and by analyzing the obtained ESR spectrum, it is possible to identify and quantitate the substance having the unpaired electron, which is referred to as free radical.

The ESR technique is also used in MRI (Magnetic Resonance Imaging). In the MRI, a magnetic field is swept while a human body is irradiated with a microwave of a constant frequency to thereby cause a magnetic resonance on hydrogen nucleus at a site to be observed. In contrast, in the present embodiment, instead of sweeping a magnetic field, a microwave (a radio wave) is swept to thereby cause a magnetic resonance on water molecules or hemoglobin molecules, which constitute the blood. The radio wave strikes against the human body to cause the magnetic resonance, and the change of the amplitude of the radio wave bounced back is detected as the pulse signal.

In the following paragraphs, a configuration example of the pulse detection apparatus 1 will be described with reference to the block diagram shown in FIG. 2. The pulse detection apparatus 1 includes the magnet 11, a VCO 12, a power amplifier 13, and a directional coupler 14; wherein the VCO 12 serves as a frequency variable oscillator, and the directional coupler 14 serves as a signal separator. The pulse detection apparatus 1 further includes a loop antenna 15T for transmitting radio wave, a loop antenna 15R for receiving radio wave, an amplitude detector 16, a phase comparator 17, and an oscillation frequency controller 18. The pulse detection apparatus 1 further includes a pulse detector 19, an adaptive filter 20, a delay circuit 21, and an adder 22.

As described above, the magnet 11 is adapted to apply the constant magnetic field to the body of the subject Sb seated on the seat St (see FIG. 1), and the magnetic strength of the magnetic field is, for example, around 0.14 tesla. In the example shown in FIG. 1, the size of the magnet 11 is designed to have an area approximately to the same the area of the palm of a human hand. However, the size of the magnet 11 is not particularly limited as long as the size is not smaller than 1 cm². The present embodiment is described using an example in which the magnet 11 is arranged below the seat St so that it is close to the buttock of the subject Sb; however, the present invention is not limited to this example. For example, the magnet 11 may be mounted to a seat belt (not shown) such that the magnet 11 becomes close to the chest or abdomen of the subject Sb. The present embodiment is described using an example in which the magnet 11 is used as the magnetic-field application unit; however, the present invention is not limited to this example, but an electromagnet may be used instead.

The VCO 12 generates an oscillation signal (a Sin wave) having an oscillation frequency corresponding to a control voltage applied from the oscillation frequency controller 18, which is to be described later, and supplies the generated oscillation signal to the power amplifier 13. The oscillation frequency at a start of operating the VCO 12 is either set to around 2.4 GHz when aiming at the water molecules in the blood, or set to around 64 MHz when aiming at the hemoglobin molecules. Thereafter, the VCO 12 generates the oscillation signal having the oscillation frequency corresponding to the control voltage applied from the oscillation frequency controller 18. The power amplifier 13 amplifies the oscillation signal supplied from the VCO 12 and supplies the amplified oscillation signal to the directional coupler 14 and the phase comparator 17.

The directional coupler 14 is connected to the loop antenna 15T and the loop antenna 15R. The directional coupler 14 cancels, among the signals outputted from the VCO 12, a signal that transmits through the air and plunged into through the loop antenna 15R for reception, and cancels, among the signals radiated from the loop antenna 15T, a signal directly picked up by the loop antenna 15R. That is, the directional coupler 14 transmits only a transmission signal and a reception signal; wherein the transmission signal is a signal inputted from the power amplifier 13 and transmitted from the loop antenna 15T, and reception signal is a radio wave transmitted from the loop antenna 15T, reflected by the subject Sb and then returned to and received by the loop antenna 15R. The transmission signal is transmitted to the loop antenna 15T. The reception signal is supplied to the amplitude detector 16 and the phase comparator 17.

The present embodiment is described using an example in which the directional coupler 14 is used as the signal separator; however, the present invention is not limited to this example, but other circuit, such as a circulator, may be used as the signal separator. In the example shown in FIG. 2, two loop antennas (i.e., the loop antenna 15T for transmission and the loop antenna 15R for reception) are provided as the loop antenna 15; however, there is also a possible configuration in which one antenna is used for performing both transmission and reception.

The amplitude detector 16 is adapted to detect the change of the amplitude of the reception signal received by the loop antenna 15R via the directional coupler 14, and is configured by, for example, a peak detector. When the water molecules or the hemoglobin molecules, which are contained in the blood of the subject Sb, generate the magnetic resonance, the amplitude of the reception signal also increases. Accordingly, when the resonance occurs, the maximum value of the amplitude signal outputted from the amplitude detector 16, which is configured as the peak detector, also increases.

The phase comparator 17 is adapted to compare the phase of the transmission signal of the loop antenna 15T with the phase of the reception signal of the loop antenna 15R. The phase comparator 17 supplies the oscillation frequency controller 18 with a phase difference signal corresponding to the phase difference between the transmission signal and the reception signal. Incidentally, a synchronous detector may be used instead of the phase comparator.

The oscillation frequency controller 18 adjusts the magnitude of the control voltage applied to the VCO 12 based on the phase difference signal, which is outputted from the phase comparator 17, and the amplitude signal, which is outputted from the amplitude detector 16. In more details, first, the oscillation frequency controller 18 sweeps the oscillation frequency oscillated by the VCO 12. When the output from the amplitude detector 16 becomes equal to or more than a predetermined level and the phase difference signal, which is the output from the phase comparator 17, becomes zero, the oscillation frequency controller 18 will stop sweeping. The oscillation frequency controller 18 causes a PLL circuit (which is configured including the phase comparator 17 and the VCO 12) to function to perform a feedback control so that the value of the output (the phase difference signal) from the phase comparator 17 becomes zero.

Figure 3A:
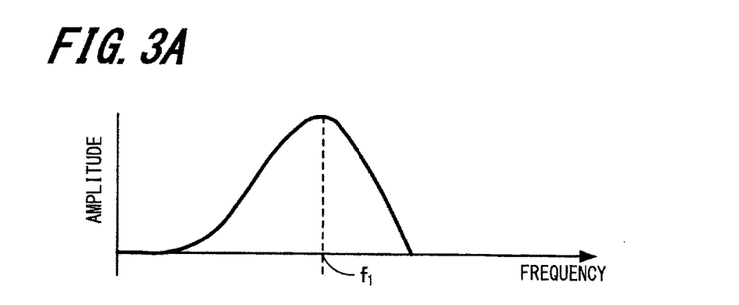
FIGS. 3A and 3B are graphs for explaining a comparison between the magnitude of the output (i.e., the amplitude) of an amplitude detector and the output of a phase comparator (i.e., the phase difference between two signals), according to the embodiment of the present invention, wherein the horizontal axis represents frequency.
Figure 3B:
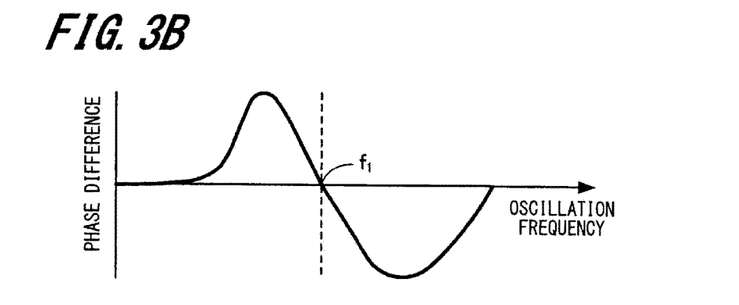

FIG. 3A and FIG. 3B are graphs for comparing the output from the amplitude detector 16 with the output from the phase comparator 17, wherein the horizontal axis represents the oscillation frequency of the VCO 12. FIG. 3A shows the output from the amplitude detector 16, which represents the amplitude value of the reception signal of the loop antenna 15R. FIG. 3B shows the output from the phase comparator 17, which represents the phase difference between the transmission signal transmitted from the loop antenna 15T and the reception signal received by the loop antenna 15R. As shown in FIG. 3A, when the water molecules or the hemoglobin molecules contained in the blood of the subject Sb cause the magnetic resonance, the amplitude of the signal outputted from the amplitude detector 16 reaches its peak at a resonance frequency $f_1$. Further, as shown in FIG. 3B, the phase difference signal outputted from the phase comparator 17 becomes zero at the resonance frequency $f_1$. That is, the phase difference between the transmission signal and the reception signal becomes zero.

When the magnitude of the reception signal passing through the amplitude detector 16, namely, the amplitude signal, becomes equal to or more than the predetermined level and the value of the phase difference signal becomes zero, the PLL circuit is functioned. This controls the phase difference signal to be zero thereafter. Thus, it is possible for the oscillation frequency of the VCO 12 to precisely follow the resonance frequency $f_1$ of the water molecules or the hemoglobin molecules, which differs depending on the subject Sb.

Figure 2:
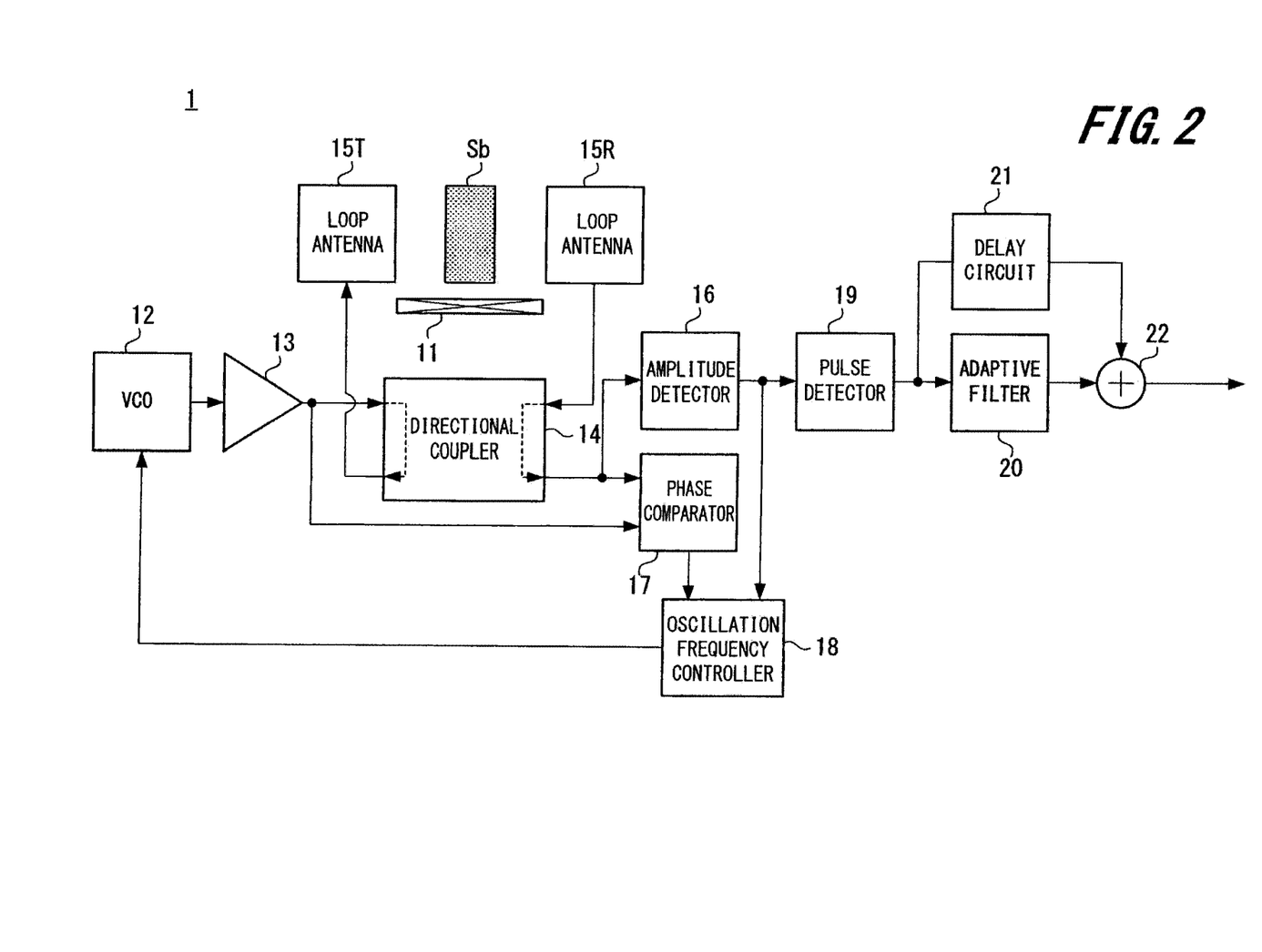
FIG. 2 is a block diagram showing a configuration example of the pulse detection apparatus according to the embodiment of the present invention.

Now back to FIG. 2 to continue the description. The pulse detector 19 is configured by, for example, a HPF (High Pass Filter). The pulse detector 19 extracts only a predetermined high-frequency component from the output of the amplitude detector 16 and outputs the high-frequency component to the adaptive filter 20 and the delay circuit 21. The cutoff frequency of the pulse detector 19 is set to, for example, 0.5 Hz or more, wherein 0.5 Hz corresponds to "30", which is considered as the lowest pulse rate of a healthy human. Therefore, it is possible to extract only the variation amount of the amplitude of the reception signal caused by the change in blood flow. In other words, it is possible to detect the pulse signal.

The adaptive filter 20 is configured by, for example, a KMS (Least Mean Square) filter. Among input signals, only a signal with predetermined periodicity is passed through the adaptive filter 20 so as to be outputted to the adder 22. By passing the signals through the adaptive filter 20 whose coefficient has been set so that only the signal having a frequency identical to the pulse (also referred to as a "pulse wave frequency" hereinafter) is allowed to pass through, it is possible to obtain a signal where an amplitude portion changed by the pulse is emphasized.

The delay circuit 21 adds a delay to the output of the pulse detector 19 and outputs the result to the adder 22, wherein the delay is equivalent to the processing time of the adaptive filter 20.

Figure 4A:
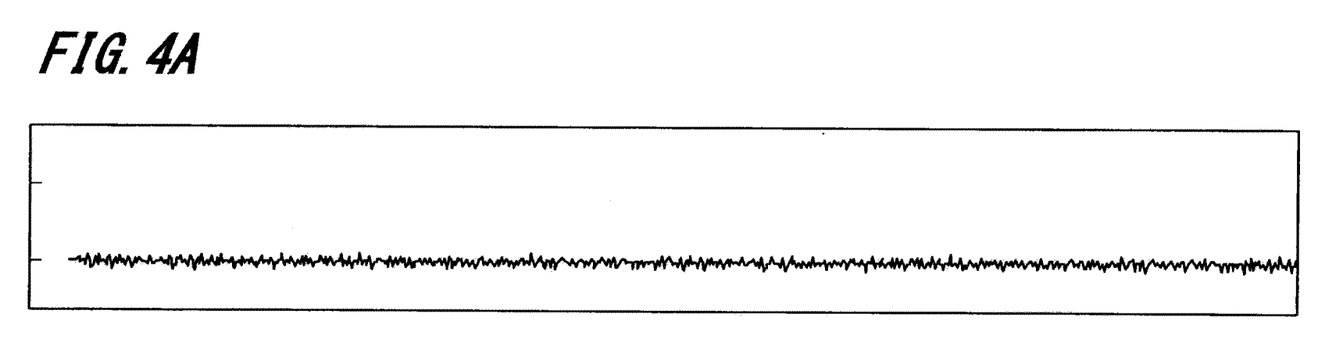
FIGS. 4A and 4B are waveform diagrams showing time-base waveforms of the output from the amplitude detector and signals passing through an adaptive filter, according to the embodiment of the present invention.
Figure 4B:
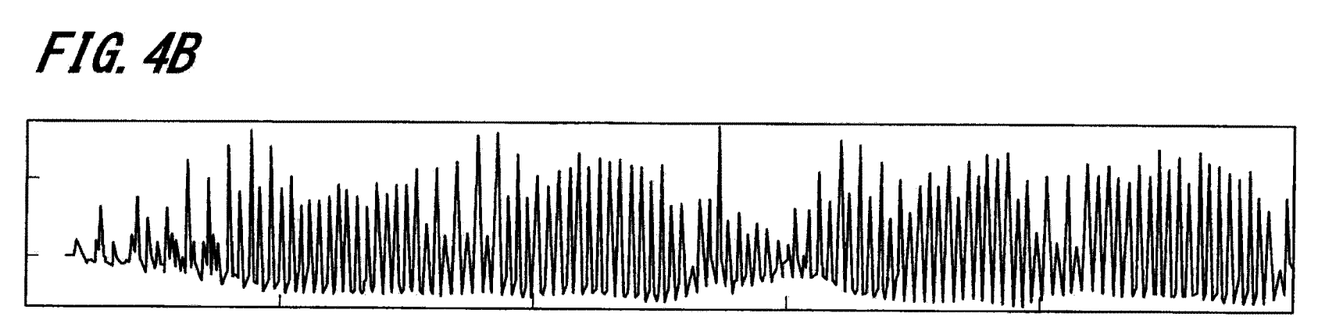

FIG. 4A and FIG. 4B are waveform diagrams showing the signals inputted to the adaptive filter 20 and the signals outputted from the adaptive filter 20. FIG. 4A shows the waveform of the signals inputted to the adaptive filter 20, and FIG. 4B shows the waveform of the signals outputted from the adaptive filter 20. In FIG. 4A and FIG. 4B, the vertical axis represents the amplitude, and the horizontal axis represents time. The signals inputted to the adaptive filter 20 (i.e., the signals outputted from the amplitude detector 16 (see FIG. 2)) shown in FIG. 4A, as a whole, have small change in amplitude; whereas the signals whose amplitude is amplified after passing through the adaptive filter 20, as shown in FIG. 4B, are signals from which noise has been removed, and therefore the amplitude thereof is emphasized.

The pulse can be measured by detecting the peak of the amplitude of the signals outputted from the adder 22 and obtaining the period of the appearance of the peak.

With the present embodiment described above, it is possible to use the ESR technique to detect the pulse signal of the subject Sb by arranging the magnet 11, the loop antenna 15T and the loop antenna 15R near the subject Sb. When detecting the pulse signal, the frequency of the radio wave irradiated on the subject Sb, instead of the magnetic field applied to the subject, is variable; therefore, the production cost of the apparatus can be reduced compared with an apparatus which sweeps the magnetic field, such as an MRI.

Also, the production cost of the apparatus can be reduced compared with the case where the Doppler method is used. Since a Doppler sensor used in the Doppler method uses a high frequency of 20 GHz, for example, typically a waveguide technique is applied; therefore, it is difficult to reduce production cost. In contrast, since the frequency used by the pulse detection apparatus 1 of the present invention is a low frequency of around 60 MHz, which falls within a frequency band also used for FM radio broadcast, the pulse detection apparatus 1 of the present invention can be produced at a low cost almost the same as the cost for producing a FM radio broadcasting receiver.

Further, since the present embodiment described above does not use the Doppler method, it is possible to relatively precisely detect the pulse even in the case where the body of the subject Sb is in motion, such as when the subject Sb is walking, driving a vehicle, or the like.

Figure 5:
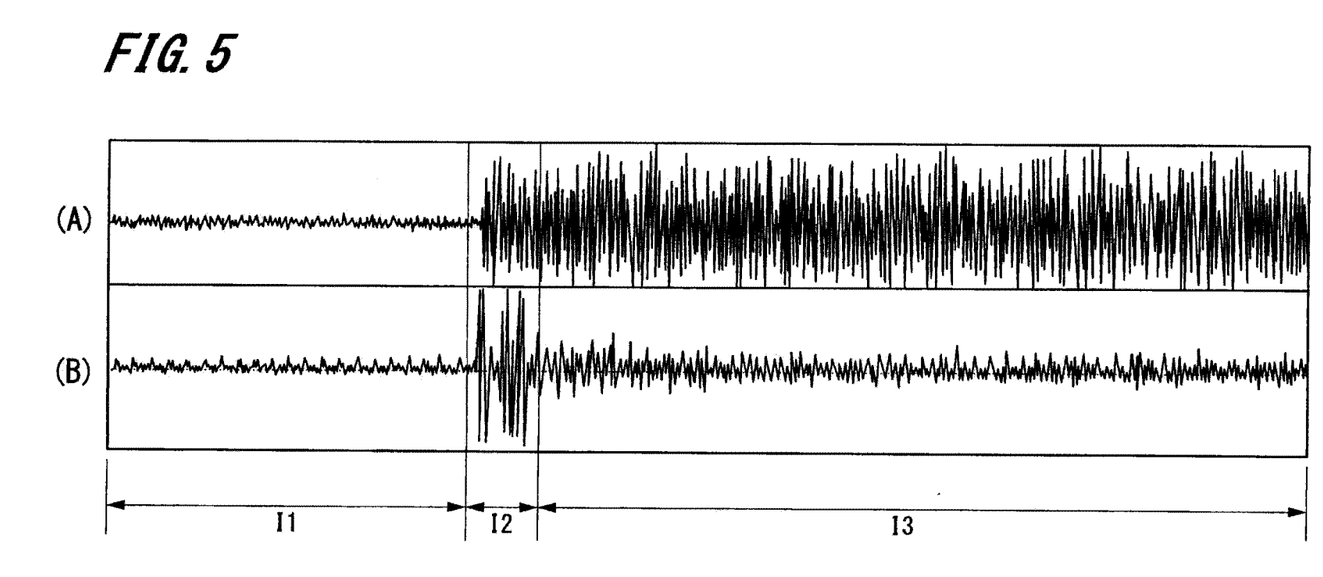
FIG. 5 are waveform diagrams showing time-base waveforms of amplitude signals detected by a Doppler method and amplitude signals detected by the amplitude detector according to the embodiment of the present invention.

Part (A) of FIG. 5 is a waveform diagram showing the amplitude signals detected by the pulse detection apparatus using the Doppler sensor. Part (B) of FIG. 5 is a waveform diagram showing the amplitude signals detected by the amplitude detector 16 of the pulse detection apparatus 1 of the present embodiment.

In each of parts (A) and (B) of FIG. 5, the vertical axis represents the amplitude while the horizontal axis represents the time. The time of the horizontal axis is constituted of an interval I1, an interval I2, and an interval I3. The interval I1 is an interval during which the subject Sb is seated on a chair and remains motionless. The interval I2 is an interval during which the subject Sb is standing up from the chair. The interval I3 is an interval during which the subject Sb keeps stepping on the spot.

The pulse detection by the Doppler method is performed in a condition where the Doppler sensor is placed at a position about 30 cm away from the subject Sb. The pulse detection by the pulse detection apparatus 1 of the present embodiment is performed in a condition where the magnet 11, the loop antenna 15T, and the loop antenna 15R are attached onto clothing in the back portion of the subject Sb.

In the amplitude signal obtained by the Doppler method, as shown in part (A) of FIG. 5, fluctuation of the amplitude in the interval I3 is considerably wild, and it is almost impossible to observe the change of the amplitude in the time direction (i.e., the periodicity cannot be confirmed). This is because, since the sensor of the Doppler method is adapted to measure the relative movement between body cells of the subject Sb and the sensor, not only the movement of the heart but also the movement of the body are detected.

In contrast, in the amplitude signal obtained by the pulse detection apparatus 1 according to the present embodiment, as shown in part (B) of FIG. 5, it is possible to observe the change of the amplitude in the time direction even in the interval I3. Accordingly, it is possible to detect the pulse by removing noise from the amplitude signal. In other words, with the pulse detection apparatus 1 according to the present embodiment, it is possible to detect the pulse even when the subject Sb is in motion (the interval I3).

Further, in the present embodiment, since Doppler method is not used, it is not necessary to consider the influence of the noise generated by the movement of the body of the subject Sb. Thus, the arrangement positions of the magnet 11, the loop antenna 15T, and the loop antenna 15R, which configure the sensor portion, do not have to be close to the heart of the subject Sb; and also, the arrangement positions do not have to be fixed. Thus, it is possible to mount the sensor portion to the body of the subject Sb who is in motion, to mount the sensor portion below the seat of the vehicle, or to mount the sensor portion under a bed.

For example, as shown in FIG. 1, by mounting the sensor portion to the seat portion of the vehicle, it is possible to quickly detect change in pulse occurring when the subject Sb behind the wheel dozes or fatigues. Thus, it is possible to establish a system that feeds back detection content to the subject Sb when doze and/or fatigue accumulation of the subject Sb has been detected by using the pulse detection apparatus 1 of the present invention.

Further, it is possible to detect the pulse signal of the subject Sb in the bed by mounting the sensor portion to the bed portion or the like. Thus, it is possible to easily and permanently detect the pulse signal of the subject Sb without putting strain on the body of the subject Sb, in the case where the subject Sb is a person whose condition is suddenly changed or whose health condition need to be maintained, such as a hospitalized patient, an aged person who lives alone, or the like.

[2. Various Modifications]

In the present embodiment described above, the adaptive filter 20 is used to generate a signal in which the pulse period is emphasized; however, such a process is not an indispensable process, and the present invention also includes a possible configuration in which the adaptive filter 20 is not used.

(Modification 1)

The aforesaid embodiment is described using an example in which the pulse signal is detected based on the amplitude detected by the amplitude detector 16; however, the present invention is not limited thereto. It is also possible to measure transfer characteristics of the loop antenna 15T and the loop antenna 15R, and detect characteristic change of the obtained transfer characteristics to thereby detect the pulse signal. For example, an S parameter can be used as the transfer characteristics. The S parameter is a parameter that indicates changes in amplitudes and phases of an incident signal and a reflected signal, and can be calculated based on the values of electric powers inputted to/outputted from the directional coupler 14 (see FIG. 2).

Figure 6:
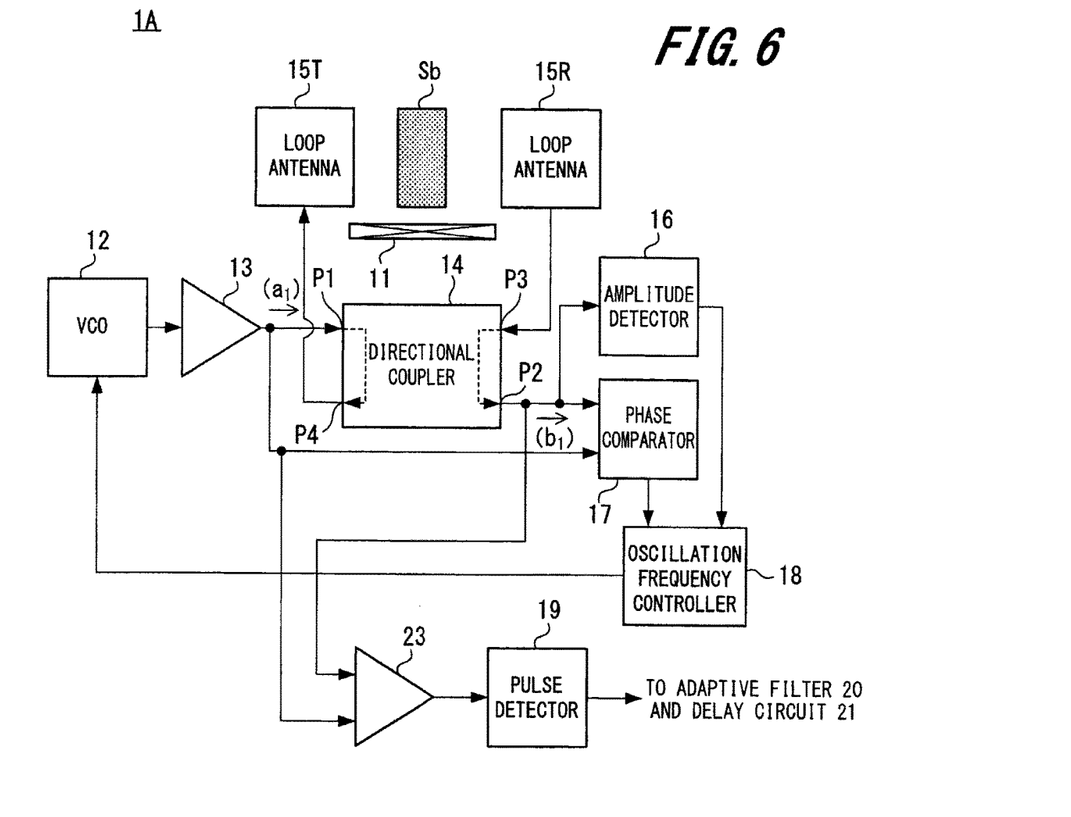
FIG. 6 is a block diagram showing a configuration example of a pulse detection apparatus according to a modification 1 of the present invention.

FIG. 6 is a block diagram showing a configuration in which an input reflection coefficient ($S_{11}$), which is an example of the S parameter, is calculated, and the change of the calculated $S_{11}$ in the time direction is detected as the pulse signal. In FIG. 6, like components are denoted by like reference numerals as of FIG. 2, and the explanation thereof will not be repeated. Note that, in a pulse detection apparatus 1A shown in FIG. 6, the adaptive filter 20, the delay circuit 21, and the adder 22 are not shown, although these components are shown in FIG. 2.

Among four ports of the directional coupler 14, a port to which a signal generated by the VCO 12 and amplified by the power amplifier 13 is inputted is referred to as a port P1; a port from which a signal transmitted to the amplitude detector 16 and the phase comparator 17 is outputted is referred to as a port P2; a port to which a signal received by the loop antenna 15R is inputted is referred to as a port P3; and a port from which a signal supplied to the loop antenna 15T is outputted is referred to as a port P4.

$S_{11}$, the input reflection coefficient, is indicated as a ratio of a reflected signal $b_1$ outputted from the port P2 to an incident signal $a_1$ inputted to the port P1. The ratio of the reflected signal $b_1$ to the incident signal $a_1$ can be calculated by a transfer function calculator 23 shown in FIG. 7. The transfer function calculator 23 includes an amplitude detector 23a, an amplitude detector 23b, and a divider 23c, wherein the amplitude detector 23a and the amplitude detector 23b detect a peak value of the input signal, and the divider 23c divides an output value from the amplitude detector 23a by an output value from the amplitude detector 23b. The amplitude detectors 23a and 23b are configured by, for example, a peak detector.

Figure 7:
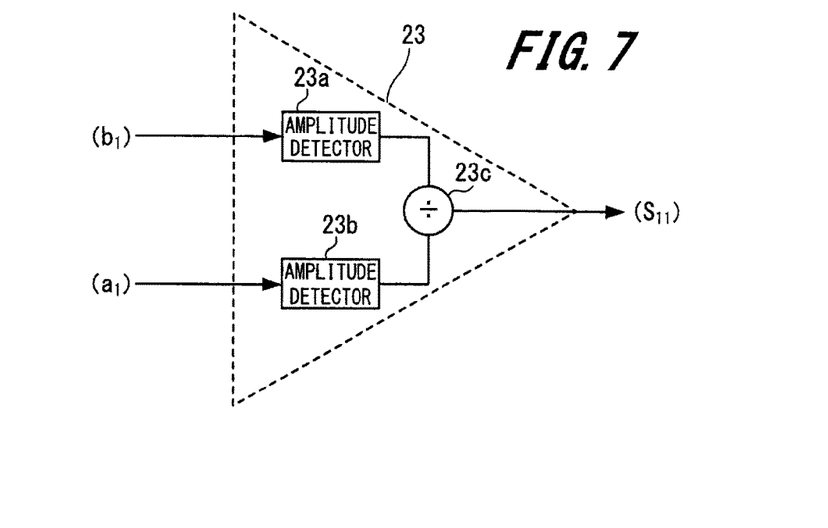
FIG. 7 is a block diagram showing a configuration example of a transfer function calculator according to the modification 1 of the present invention.

The incident signal $a_1$, which is inputted to the port P1 shown in FIG. 6, is inputted to the amplitude detector 23b shown in FIG. 7, and the reflected signal $b_1$, which is outputted from the port P2, is inputted to the amplitude detector 23a, so that "reflected signal $b_1$/incident signal $a_1=S_{11}$" is outputted from the transfer function calculator 23. The calculated $S_{11}$ is inputted to the pulse detector 19, and thereby only the change of the characteristic of $S_{11}$ is outputted from the pulse detector 19. The change of $S_{11}$ in an amplitude direction occurs corresponding to the variation of pulse. Accordingly, when $S_{11}$ passes through the pulse detector 19, the variation can be extracted as the pulse signal.

Figure 8A:
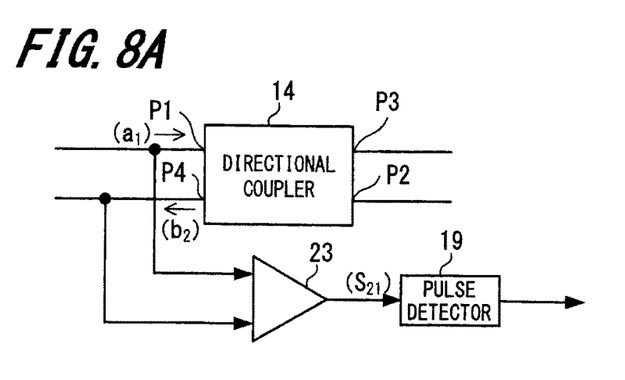
FIG. 8A, FIG. 8B, and FIG. 8C are block diagrams each showing an exemplary coupling of a directional coupler and the transfer function calculator according to the modification 1 of the present invention.
Figure 8B:
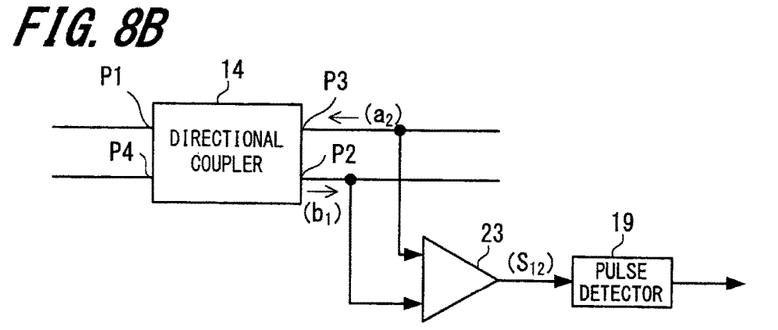
Figure 8C:
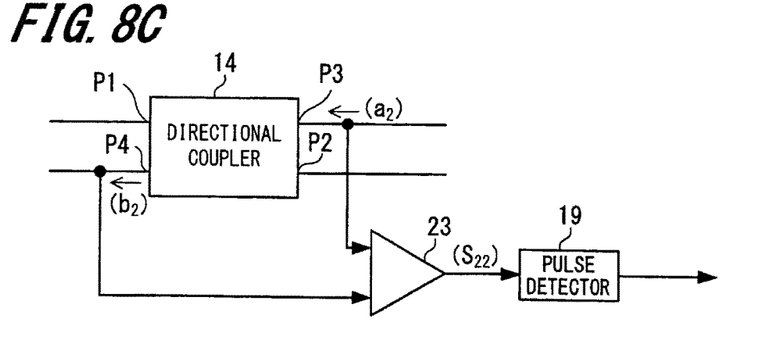

The S parameter used for detecting the period of the pulse is not limited to the input reflection coefficient ($S_{11}$). Any one of a forward direction transfer coefficient ($S_{21}$), a reverse direction transfer coefficient ($S_{12}$), and an output reflection coefficient ($S_{22}$) may also be used as the S parameter. FIG. 8A shows a configuration example of obtaining the forward direction transfer coefficient ($S_{21}$); FIG. 8B shows a configuration example of obtaining the reverse direction transfer coefficient ($S_{12}$); and FIG. 8C shows a configuration example of obtaining the output reflection coefficient ($S_{22}$). Components other than the directional coupler 14, the transfer function calculator 23, and the pulse detector 19 are not shown in FIG. 8A to FIG. 8C; however, it should be noted that the components not shown in FIG. 8A to FIG. 8C have the same configuration as those shown in FIG. 6.

$S_{21}$, the forward direction transfer coefficient, is indicated as a ratio of a reflected (transmission) signal $b_2$ outputted from the port P4 to the incident signal $a_1$ inputted to the port P1. As shown in FIG. 8A, the incident signal $a_1$, which is inputted to the port P1, and the reflected signal $b_2$, which is outputted from the port P4, are inputted to the transfer function calculator 23, so that "transmission signal $b_2$/incident signal $a_1=S_{21}$" is outputted from the transfer function calculator 23.

$S_{12}$, the reverse direction transfer coefficient, is indicated as a ratio of the reflected (transmission) signal $b_1$ outputted from the port P2 to an incident signal $a_2$ inputted to the port P3. As shown in FIG. 8B, the incident signal $a_2$, which is inputted to the port P3, and the reflected signal $b_1$, which is outputted from the port P2, are inputted to the transfer function calculator 23, so that "reflected signal $b_1$/incident signal $a_2=S_{12}$" is outputted from the transfer function calculator 23.

$S_{22}$, the output reflection coefficient, is indicated as a ratio of the reflected signal $b_2$ outputted from the port P4 to the incident signal $a_2$ inputted to the port P3. As shown in FIG. 8C, the incident signal $a_2$, which is inputted to the port P3, and the reflected signal $b_2$, which is outputted from the port P4, are inputted to the transfer function calculator 23, so that "reflected signal $b_2$/incident signal $a_2=S_{22}$" is outputted from the transfer function calculator 23. In such a manner, it is also possible to detect the pulse signal by using the S parameter, which indicates the transfer characteristics of the loop antenna 15T and the loop antenna 15R.

(Modification 2)

The above-described present embodiment is described using an example in which the pulse detection apparatus 1 (or the pulse detection apparatus 1A) is mounted in the vehicle; however, the present invention is not limited thereto. The pulse detection apparatus of the present invention may be applied to any form as long as the form allows detection of data sufficient for detection of the pulse. The form allowing detection of data sufficient for detection of the pulse is achieved by, for example, arranging the sensor portion, which is configured by the magnet 11, the loop antenna 15T, and the loop antenna 15R, at a position close to the body of the subject Sb.

Figure 9:
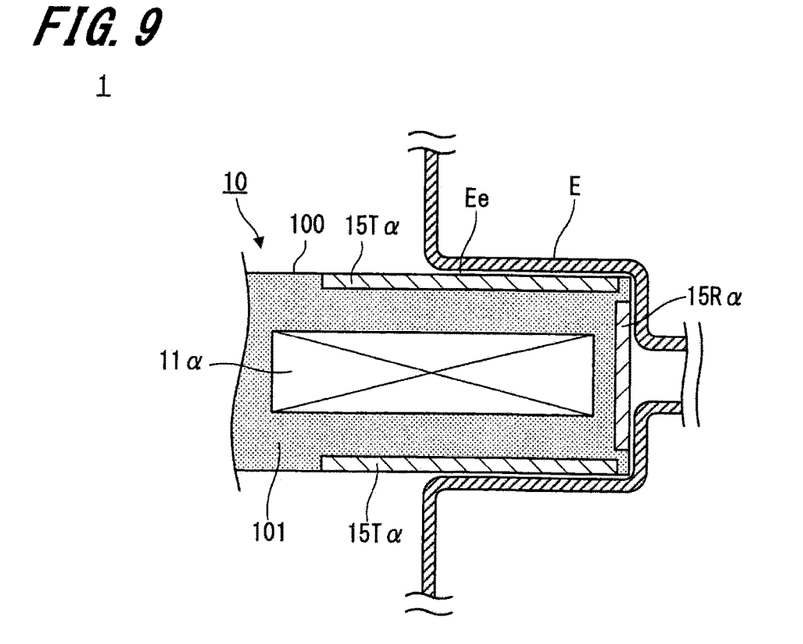
FIG. 9 is a schematic diagram showing another configuration example of a sensor portion of the pulse detection apparatus according to the modification 1 of the present invention.

FIG. 9 shows an example in which the sensor portion of the pulse detection apparatus 1 is configured as an earphone-type sensor. Incidentally, FIG. 9 shows only the sensor portion of the pulse detection apparatus 1. In FIG. 9, the sensor portion is shown as an "earphone-type sensor 10." The earphone-type sensor 10 includes a casing 100, a magnet 11α, loop antennas 15Tα, and a loop antenna 15Rα, wherein the casing 100 is to be inserted into an ear E of the subject Sb, and the magnet 11α, the loop antennas 15Tα, and the loop antenna 15Rα are arranged within the casing 100.

Specifically, the loop antennas 15Tα for transmitting radio wave are arranged on the top surface and the bottom surface in the casing 100. The loop antenna 15Rα for receiving radio wave is arranged in an end portion of the casing 100 in an insertion direction into the external auditory canal Ee. By arranging each loop antenna in such a manner, when the earphone-type sensor 10 is inserted into the ear E of the subject Sb, each of these antennas comes in contact with or close to the skin of the side surface of the external auditory canal Ee of the ear E.

The magnet 11α is arranged in a central portion of the casing 100, and the space between the resin 101 and the loop antenna 15Tα and loop antenna 15Rα is filled with a resin 101, such as plastic; and thereby the influence of the magnet 11α on each antenna can be reduced. The magnet 11α is substantially formed into a rectangular parallelepiped-shape whose longitudinal direction is identical to the formation direction of the external auditory canal Ee, and thereby the distance between the skin of the side surface of the external auditory canal Ee and the magnet 11α in the diametrical direction of the external auditory canal Ee can be reduced.

By arranging the magnet 11α, the loop antenna 15Tα, and the loop antenna 15Rα in the aforesaid manner, not only the magnetic field and the radio wave for performing detection of the pulse become easy to reach the body of the subject Sb, but also it becomes easy to receive the radio wave reflected by the body of the subject Sb. Further, since the sensor portion of the pulse detection apparatus 1 is configured as the earphone-type sensor 10, the pulse of the subject Sb can be easily detected simply by inserting the earphone-type sensor 10 into the ear E of the subject Sb.

The pulse detection apparatus 1 (or 1A) of the present invention is also applicable to a blood pressure measuring apparatus. For example, a sensor unit of the pulse detection apparatus 1 (or 1A) is arranged at a side surface of a cuff, which presses so as to obstruct the artery, on a side in contact with an arm of the subject Sb, so that it is possible to detect the pulse wave generated at the blood vessel wall as the pulse signal in a process of depressurizing the cuff. Then, by using a blood pressure measurement technique by oscillometric method, the blood pressure of the subject Sb can be measured based on the detected pulse wave.

REFERENCE SIGNS LIST 1, 1A pulse detection apparatus
11 magnet
12 VCO
13 power amplifier
14 directional coupler
15, 15R, 15T loop antenna
16 amplitude detector
17 phase comparator
18 oscillation frequency controller
19 HPF
20 adaptive filter

The invention claimed is:

1. A pulse detection apparatus, comprising:
a magnetic-field application unit to be arranged near a human body to apply a predetermined magnetic field to the human body;
a frequency variable oscillator configured to oscillate at a predetermined oscillation frequency, the predetermined oscillation frequency being a frequency within a range assumed as a resonance frequency of a molecule of a predetermined constituent constituting the blood flowing through the human body;
an antenna arranged near the human body and configured to transmit a signal oscillated by the frequency variable oscillator, as a radio wave, and receive a radio wave reflected by the human body and then returned to the antenna;
a signal separator configured to separate a transmission signal from a reception signal, the transmission signal being transmitted from the antenna, the reception signal being received by the antenna;
a phase comparator configured to compare the phase of the transmission signal with the phase of the reception signal and output a phase difference signal;
an amplitude detector configured to detect the amplitude of the reception signal and output an amplitude signal related to a pulse of the human body;
an oscillation frequency controller configured to control the oscillation frequency of the frequency variable oscillator based on the phase difference signal and the amplitude signal; and
a pulse detector configured to calculate the pulse of the human body using a change of the amplitude signal in an amplitude direction.

2. The pulse detection apparatus according to claim 1, wherein the pulse detector includes a high pass filter that allows signal(s) with a frequency equal to or higher than a frequency corresponding to the period of the pulse to pass through.

3. The pulse detection apparatus according to claim 1, wherein if the amplitude detector detects an amplitude equal to or greater than a predetermined level and the value of the phase difference signal is zero, the oscillation frequency controller will cause a PLL controller to function to control the oscillation frequency so that the value of the phase difference signal is maintained at zero.

4. The pulse detection apparatus according to claim 3, further comprising:
an adaptive filter configured to pass through, among the signal(s) having passed through the pulse detector, only a signal having a pulse wave frequency, wherein the pulse wave frequency is a frequency identical to the frequency of the pulse.

5. A pulse detection apparatus, comprising:
a magnetic-field application unit to be arranged near a human body to apply a predetermined magnetic field to the human body;
a frequency variable oscillator configured to oscillate at a predetermined oscillation frequency, the predetermined oscillation frequency being a frequency within a range assumed as a resonance frequency of a molecule of a predetermined constituent constituting the blood flowing through the human body;
an antenna arranged near the human body and configured to transmit a signal oscillated by the frequency variable oscillator, as a radio wave, and receive a radio wave reflected by the human body and then returned to the antenna;
a signal separator configured to separate a transmission signal from a reception signal, the transmission signal being transmitted from the antenna, the reception signal being received by the antenna;
a phase comparator configured to compare the phase of the transmission signal with the phase of the reception signal and output a phase difference signal;
a first amplitude detector configured to detect the amplitude of the transmission signal and output a first amplitude signal related to a pulse of the human body;
a second amplitude detector configured to detect the amplitude of the reception signal and output a second amplitude signal related to the pulse of the human body;

a transfer function calculator configured to use the first amplitude signal and the second amplitude signal to calculate a transfer function of the antenna;

an oscillation frequency controller configured to control the oscillation frequency of the frequency variable oscillator based on the phase difference signal and the amplitude signal; and a pulse detector configured to calculate the pulse of the human body using a change of the transfer function calculated by the transfer function calculator in an amplitude direction.

6. The pulse detection apparatus according to claim 5, wherein the transfer function is an S parameter calculated using: the transmission signal or the reception signal inputted to the signal separator, and a signal outputted from the signal separator or a signal passing through the signal separator.

7. A pulse detection method, comprising:

applying, using a magnetic-field application unit, a predetermined magnetic field to a human body;

causing a frequency variable oscillator to oscillate at a predetermined frequency, the predetermined oscillation frequency being a frequency within a range assumed as a resonance frequency of a molecule of a predetermined constituent constituting the blood flowing through the human body;

transmitting a signal oscillated by the frequency variable oscillator, as a radio wave, from an antenna arranged near the human body, and receiving a radio wave reflected by the human body and then returned to the antenna;

separating, using a signal separator, a transmission signal from a reception signal, the transmission signal being transmitted from the antenna, the reception signal being received by the antenna;

comparing, using a phase comparator, the phase of the transmission signal with the phase of the reception signal and outputting a phase difference signal;

detecting, using an amplitude detector, the amplitude of the reception signal and outputting an amplitude signal related to a pulse of the human body;

controlling, using an oscillation frequency controller, the oscillation frequency of the frequency variable oscillator based on the phase difference signal and the amplitude signal; and calculate, using a pulse detector, the pulse of the human body using a change of the amplitude signal in an amplitude direction.

* * * * *